US007998164B2

(12) United States Patent
Saholt et al.

(10) Patent No.: US 7,998,164 B2
(45) Date of Patent: Aug. 16, 2011

(54) INTRAVASCULAR FILTER WITH CENTERING MEMBER

(75) Inventors: Douglas R. Saholt, Mound, MN (US); Jay Rassat, Buffalo, MN (US); Mel R. Beulke, Bloomington, MN (US); Steven E. Peterson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1226 days.

(21) Appl. No.: 11/077,584

(22) Filed: Mar. 11, 2005

(65) Prior Publication Data
US 2006/0203769 A1    Sep. 14, 2006

(51) Int. Cl.
*A61M 29/00* (2006.01)
(52) U.S. Cl. ...................................... 606/200
(58) Field of Classification Search ............... 606/200, 606/198; 623/23.72
See application file for complete search history.

(56) References Cited

U.S. PATENT DOCUMENTS

| | | |
|---|---|---|
| 3,952,747 A | 4/1976 | Kimmell, Jr. |
| 3,996,938 A | 12/1976 | Clark, III |
| 4,425,908 A * | 1/1984 | Simon ............................ 128/899 |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A * | 2/1987 | Mobin-Uddin ............... 606/200 |
| 4,650,466 A | 3/1987 | Luther |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,817,600 A | 4/1989 | Herms et al. |
| 4,832,055 A | 5/1989 | Palestrant |
| 4,926,858 A | 5/1990 | Gifford, III et al. |
| 4,957,501 A | 9/1990 | Lahille et al. |
| 4,991,602 A | 2/1991 | Amplatz et al. |
| 4,994,069 A | 2/1991 | Ritchart et al. |
| 5,053,008 A | 10/1991 | Bajaj |
| 5,059,205 A | 10/1991 | El-Nounou et al. |
| 5,067,489 A | 11/1991 | Lind |
| 5,108,419 A | 4/1992 | Reger et al. |
| 5,152,777 A | 10/1992 | Goldberg et al. |
| 5,160,342 A | 11/1992 | Reger et al. |
| 5,256,146 A * | 10/1993 | Ensminger et al. ........... 604/104 |
| 5,324,304 A | 6/1994 | Rasmussen |
| 5,329,942 A | 7/1994 | Gunther et al. |
| 5,350,398 A | 9/1994 | Pavenik et al. |
| 5,354,310 A | 10/1994 | Garnic et al. |
| 5,375,612 A | 12/1994 | Cottenceau et al. |
| 5,490,859 A | 2/1996 | Mische et al. |
| 5,531,788 A | 7/1996 | Dible et al. |
| 5,591,197 A | 1/1997 | Orth et al. |
| 5,626,605 A | 5/1997 | Irie et al. |

(Continued)

*Primary Examiner* — Darwin P Erezo
*Assistant Examiner* — Dianne Dornbusch
(74) *Attorney, Agent, or Firm* — Seager, Tufte & Wickhem LLC

(57) ABSTRACT

Devices and methods for centering an intravascular filter within a blood vessel are disclosed. A filter system in accordance with an exemplary embodiment of the present invention may include an intravascular filter, a filter sheath adapted to contain the intravascular filter, and a centering member adapted to assume a preset shape when deployed within a blood vessel. The centering member may comprise an elongated wire having a hoop section adapted to radially expand against the inner wall of the blood vessel when deployed. In some embodiments, multiple centering members can be employed to facilitate centering of both the intravascular filter and the filter sheath within the blood vessel, if desired.

21 Claims, 13 Drawing Sheets

U.S. PATENT DOCUMENTS

| | | |
|---|---|---|
| 5,634,942 A | 6/1997 | Chevillon et al. |
| 5,669,933 A | 9/1997 | Simon et al. |
| 5,681,347 A | 10/1997 | Cathcart et al. |
| 5,683,411 A | 11/1997 | Kavteladze et al. |
| 5,690,671 A | 11/1997 | McGurk et al. |
| 5,695,519 A | 12/1997 | Summers et al. |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,769,816 A | 6/1998 | Barbut et al. |
| 5,776,162 A | 7/1998 | Kleshinski |
| 5,795,322 A | 8/1998 | Boudewijn |
| 5,810,874 A | 9/1998 | Lefebvre |
| 5,814,064 A | 9/1998 | Daniel et al. |
| 5,827,324 A * | 10/1998 | Cassell et al. ................ 606/200 |
| 5,836,868 A | 11/1998 | Ressemann et al. |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,897,567 A | 4/1999 | Ressemann et al. |
| 5,910,154 A | 6/1999 | Tsugita et al. |
| 5,911,717 A | 6/1999 | Jacobsen et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,951,585 A | 9/1999 | Cathcart et al. |
| 5,957,949 A | 9/1999 | Leonardt et al. |
| 5,968,071 A | 10/1999 | Chevillon et al. |
| 5,976,172 A | 11/1999 | Homsma et al. |
| 5,980,555 A | 11/1999 | Barbut et al. |
| 5,984,947 A | 11/1999 | Smith |
| 5,989,281 A | 11/1999 | Barbut et al. |
| 6,001,118 A | 12/1999 | Daniel et al. |
| 6,007,558 A | 12/1999 | Ravenscroft et al. |
| 6,013,093 A | 1/2000 | Nott et al. |
| 6,027,520 A | 2/2000 | Tsugita et al. |
| 6,042,598 A | 3/2000 | Tsugita et al. |
| 6,053,932 A | 4/2000 | Daniel et al. |
| 6,059,814 A | 5/2000 | Ladd |
| 6,059,825 A | 5/2000 | Hobbs et al. |
| 6,063,113 A | 5/2000 | Kavteladze et al. |
| 6,066,149 A | 5/2000 | Samson et al. |
| 6,066,158 A | 5/2000 | Engelson et al. |
| 6,068,645 A | 5/2000 | Tu |
| 6,074,357 A | 6/2000 | Kaganov et al. |
| 6,080,178 A | 6/2000 | Meglin |
| 6,086,605 A | 7/2000 | Barbut et al. |
| 6,093,199 A | 7/2000 | Brown et al. |
| 6,096,052 A | 8/2000 | Callister et al. |
| 6,096,053 A | 8/2000 | Bates |
| 6,099,549 A | 8/2000 | Bosma et al. |
| 6,117,154 A | 9/2000 | Barbut et al. |
| 6,123,715 A | 9/2000 | Amplatz |
| 6,125,946 A | 10/2000 | Chen |
| 6,126,673 A | 10/2000 | Kim et al. |
| 6,129,739 A | 10/2000 | Khosravi |
| 6,136,016 A | 10/2000 | Barbut et al. |
| 6,142,987 A | 11/2000 | Tsugita |
| 6,146,396 A | 11/2000 | Konya et al. |
| 6,152,947 A | 11/2000 | Ambrisco et al. |
| 6,165,179 A | 12/2000 | Cathcart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 8,179,859 | 1/2001 | Batas at al. |
| 6,187,025 B1 | 2/2001 | Machek |
| 6,193,739 B1 | 2/2001 | Chevillon et al. |
| 6,214,025 B1 | 4/2001 | Thistle et al. |
| 8,217,600 | 4/2001 | DiMatteo |
| 6,231,581 B1 | 5/2001 | Shank et al. |
| 6,231,589 B1 | 5/2001 | Wessman et al. |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,331,184 B1 | 12/2001 | Abrams |
| 6,342,063 B1 | 1/2002 | DeVries et al. |
| 6,342,064 B1 * | 1/2002 | Koike et al. ................ 606/213 |
| 6,344,041 B1 | 2/2002 | Kupiecki et al. |
| 6,368,338 B1 * | 4/2002 | Konya et al. ................ 606/200 |
| 6,402,771 B1 | 6/2002 | Palmer et al. |
| 6,436,121 B1 | 8/2002 | Blom |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 | 1/2003 | Goldberg et al. |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,031 B2 * | 5/2003 | Chandrasekaran et al. .... 606/41 |
| 6,562,058 B2 * | 5/2003 | Seguin et al. ................ 606/200 |
| 6,652,558 B2 | 11/2003 | Patel et al. |
| 6,660,021 B1 | 12/2003 | Palmer et al. |
| 6,755,847 B2 | 6/2004 | Eskuri |
| 6,783,538 B2 | 8/2004 | McGuckin, Jr. et al. |
| 6,793,665 B2 | 9/2004 | McGuckin, Jr. et al. |
| 6,878,153 B2 | 4/2005 | Linder et al. |
| 6,918,921 B2 | 7/2005 | Brady et al. |
| 6,951,570 B2 | 10/2005 | Linder et al. |
| 2002/0072764 A1 * | 6/2002 | Sepetka et al. ................ 606/200 |
| 2002/0099437 A1 | 7/2002 | Anson et al. |
| 2002/0116024 A1 | 8/2002 | Goldberg et al. |
| 2002/0123761 A1 | 9/2002 | Barbut et al. |
| 2002/0161393 A1 | 10/2002 | Demond et al. |
| 2003/0208227 A1 | 11/2003 | Thomas |
| 2003/0208253 A1 | 11/2003 | Beyer et al. |
| 2004/0133269 A1 | 7/2004 | Bruckheimer et al. |
| 2004/0225354 A1 * | 11/2004 | Allen et al. ................ 623/2.11 |

* cited by examiner

INTRAVASCULAR FILTER WITH CENTERING MEMBER

TECHNICAL FIELD

The present invention relates generally to the field of medical devices. More specifically, the present invention pertains to systems and methods for centering intravascular filters within the body.

BACKGROUND

Intravascular filters are typically used in combination with other thrombolytic agents to treat pulmonary embolism occurring within a patient. Such devices are generally implanted within a vessel such as the inferior or superior vena cava, and function by capturing blood clots (emboli) contained in the blood stream before they can reach the lungs and cause permanent damage to the body. To trap emboli contained within the blood, many conventional filters include an apical head operatively coupled to a plurality of elongated filter legs that can be expanded within the body to form a conical-shaped surface that captures blood clots without disturbing the flow of blood. Once collected, a natural clot lysing process occurs within the body to dissolve the blood clots collected by the filter.

Delivery of the intravascular filter within the body is generally accomplished via an introducer sheath percutaneously inserted through the femoral (groin) or jugular (neck) veins. Such introducer sheaths are typically tubular in shape, and include an interior lumen configured to transport the filter in a collapsed position through the body. Once transported to a desired location in the body, the filter can then be removed from within the introducer sheath, allowing the filter legs to spring open and engage the vessel wall. A needle, hook, barb, prong, wedge or other attachment means disposed on the free end of each filter leg can be used to secure the filter to the vessel wall.

The efficacy of the intravascular filter to capture blood clots is dependent in part on the ability of the filter to center when deployed within the blood vessel. Tilting of the filter may result if the apical head is not aligned centrally within the vessel, causing the filter legs to asymmetrically engage the vessel wall. Tilting of the filter may also result if the introducer sheath used to deploy the filter is off-centered within the blood vessel. In certain circumstances, tilting of the filter may affect the ability of the device to efficiently capture blood clots contained in the blood.

SUMMARY

The present invention pertains to systems and methods for centering intravascular filters within the body. A filter system in accordance with an illustrative embodiment of the present invention may include an intravascular filter, a filter sheath having an interior lumen adapted to contain the intravascular filter, and a centering member adapted to radially expand when deployed within a blood vessel. The centering member may comprise an elongated wire that, when unconstrained radially, assumes a preset shape having a radial section and a hoop section. The radial section may comprise a portion of the elongated wire extending outwardly in a direction substantially orthogonal to the interior wall of the blood vessel. The hoop section, in turn, may comprise a portion of the elongated wire that radially expands against the inner wall of the blood vessel. In some embodiments, a tubular member having an interior lumen can be configured to radially constrain the centering member in a substantially straight position to facilitate delivery and/or retrieval of the filter assembly through the body.

In certain embodiments, the filter system may include multiple centering members that can be used in centering the intravascular filter and/or filter sheath at multiple locations within the blood vessel. In one illustrative embodiment, for example, a second centering member may be provided at or near the distal end of the filter sheath to center the filter sheath within the blood vessel, if necessary. The second centering member may similarly comprise an elongated wire that, when unconstrained radially within a second interior lumen of the filter sheath, can be configured to assume a preset shape within the blood vessel. As with the other embodiments described herein, the second centering member may include a radial section adapted to extend outwardly in a direction substantially orthogonal to the interior wall of the blood vessel, and a hoop section adapted to radially expand against the inner wall of the blood vessel.

An illustrative method of centering an intravascular filter within a patient's blood vessel may include the steps of providing an intravascular filter and centering member within an interior lumen of a filter sheath, inserting the filter sheath into the patient and advancing the filter sheath to a desired location within the blood vessel, deploying the centering member within the blood vessel, and then deploying the intravascular filter within the blood vessel. Other methods and techniques are also described herein. As used herein proximal end distal refer to the orientation of the system as delivered by a femoral approach to the vena cava. It is understood that the system could be use in other vessels, and from other approaches.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
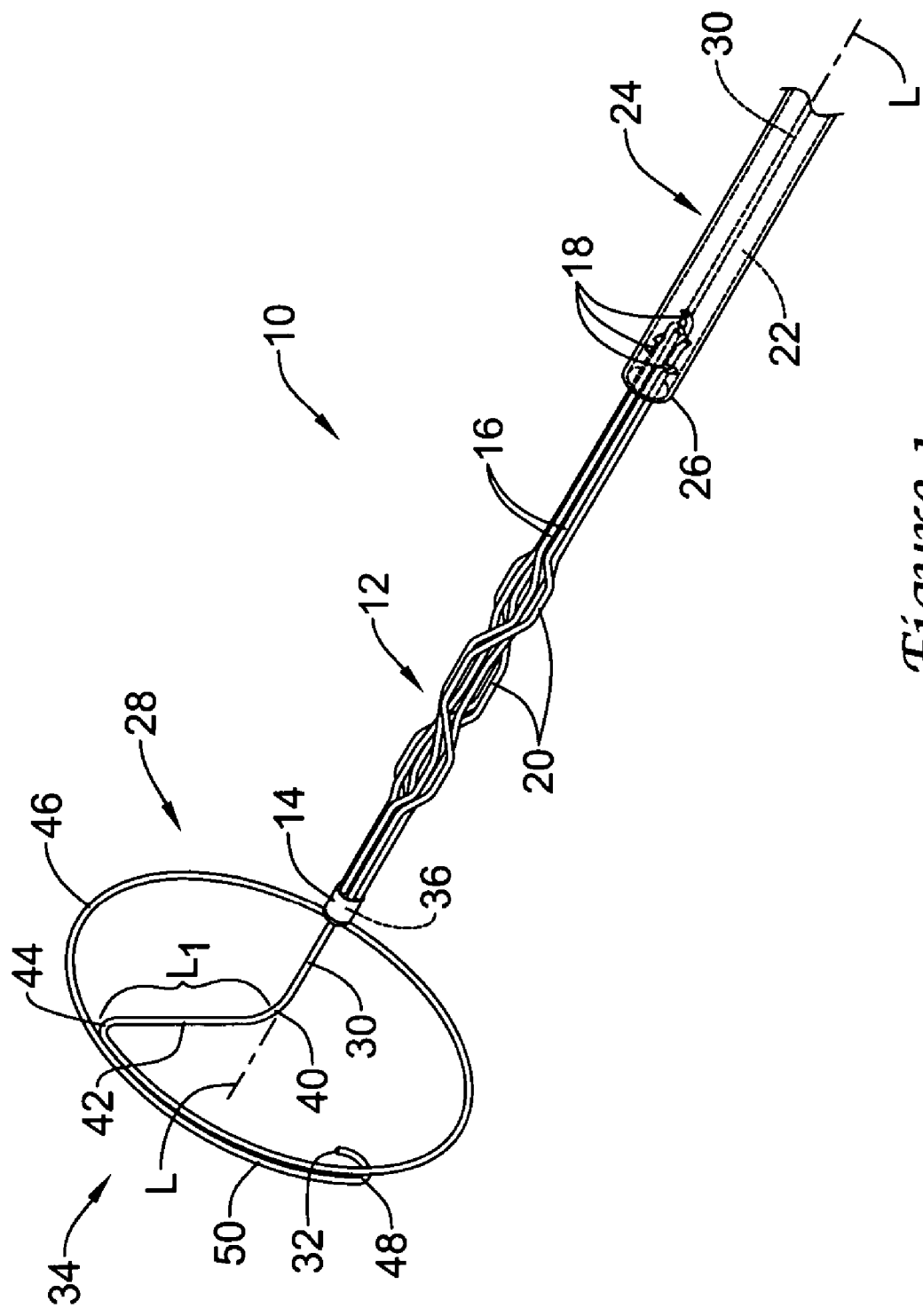
FIG. 1 is perspective view of a filter system in accordance with an illustrative embodiment of the present invention employing a single centering member.

FIG. 1 is perspective view of a filter system 10 in accordance with an illustrative embodiment of the present invention. Filter system 10, illustratively a filter system for use in the inferior and/or superior vena cava, can include an intravascular filter 12 having an apical head 14 and a plurality of elongated filter legs 16 adapted to expand and secure the intravascular filter 12 to the inner wall of a blood vessel. The free end 18 of each filter leg 16 may include a needle, hook, barb, prong, wedge or other suitable attachment means for securing the intravascular filter 12 to the inner wall of the blood vessel. A number of bend regions 20 located along the length of one or more of the filter legs 16 can also be provided to increase the surface area of the intravascular filter 12, if desired.

The filter legs 16 can be configured to radially collapse within an interior lumen 22 of a filter sheath 24 to delivery and/or receive the intravascular filter 12 through the patient's body. The filter sheath 24 may comprise a tubular member having a distal end 26 and a proximal end (not shown). For sake of clarity in FIG. 1, the intravascular filter 12 is shown withdrawn at least in part from within the interior lumen 22 of the filter sheath 24, exposing all but the free end 18 of each filter leg 16. It should be understood, however, that all or a portion of the intravascular filter 12 can be loaded within the interior lumen 22 of the filter sheath 24, if desired.

As can be further seen in FIG. 1, the filter system 10 may also include a centering member 28 that can be used to aid in centering the intravascular filter 12 within the interior of the blood vessel. The centering member 28 may comprise an elongated wire 30 having a distal end 32, a proximal end (not shown), and a distal section 34 adapted to assume a preset shape when deployed within the blood vessel. Prior to insertion within the patient's body, the elongated wire 30 can be inserted through an interior lumen 36 formed through the apical head 14 and through the interior lumen 22 of the filter sheath 24.

The distal section 34 may comprise a portion of the elongated wire 30 extending distally from a first bend region 40 of the elongated wire 30 to the distal end 32 thereof. A radial section 42 of the elongated wire 30 extending distally from the first bend region 40 can be adapted to extend outwardly in a direction substantially orthogonal to the interior wall of the blood vessel, when deployed. The length $L_1$ in which the radial section 42 extends outwardly may vary depending on the particular vessel the intravascular filter 12 is to be inserted into. In applications involving the superior or inferior vena cava, for example, the length $L_1$ of the radial section 42 may be in the range of about 6 mm to 15 mm, which is sufficient for blood vessels having a diameter of about 12 mm to 30 mm. It should be understood, however, that the length $L_1$ of the radial section 42 may vary to permit the centering member 28 to be used in other regions of the body and/or to accommodate for anatomical differences among patients.

At a second bend region 44 of the distal section 34, the radial section 42 may transition to a hoop section 46 of the elongated wire 30 extending circumferentially about a general longitudinal axis L of the intravascular filter 12 and filter sheath 24. The shape 6f the hoop section 46 can be selected to approximate the general shape of the blood vessel, allowing the hoop section 46 to radially expand and fully appose the inner wall of the blood vessel. In certain embodiments, for example, the hoop section 46 of the elongated wire 30 may have a substantially elliptical shape to facilitate centering of the intravascular filter 12 in blood vessels having an oblique or non-symmetrical shape. In other embodiments, the hoop section 46 may have a substantially circular shape to facilitate centering of the intravascular filter 12 in blood vessels having a substantially symmetrical shape.

In the illustrative embodiment of FIG. 1, the hoop section 46 is configured to lie in a single plane that is oriented substantially orthogonal to the length of the blood vessel. In an alternative embodiment, the hoop section 46 can be configured to spiral in multiple planes along the longitudinal axis L. In the latter case, for example, the hoop section 46 may have the general shape of a helix that tapers distally towards the distal end 32. The hoop section 46 may assume other desired shapes, however, to facilitate centering of the intravascular filter 12 at other locations within the body such as at a branching vessel.

At a third bend region 48 of the distal section 34, the distal end 32 of the elongated wire 30 may curl inwardly towards the longitudinal axis L. In use, the third bend region 48 orients the distal end 32 away from the inner wall of the blood vessel, preventing the distal end 32 from contacting the blood vessel. If desired, an overlapping portion 50 of the hoop section 46 wherein the elongated wire 30 is wound adjacent itself can be used to space the distal end 32 away from the second bend region 44. In some embodiments, the distal end 32 may also be rounded to further prevent trauma to the vessel wall. Also, the bend region 48 may be diametrically tapered to further prevent trauma to the vessel wall.

Figure 2:
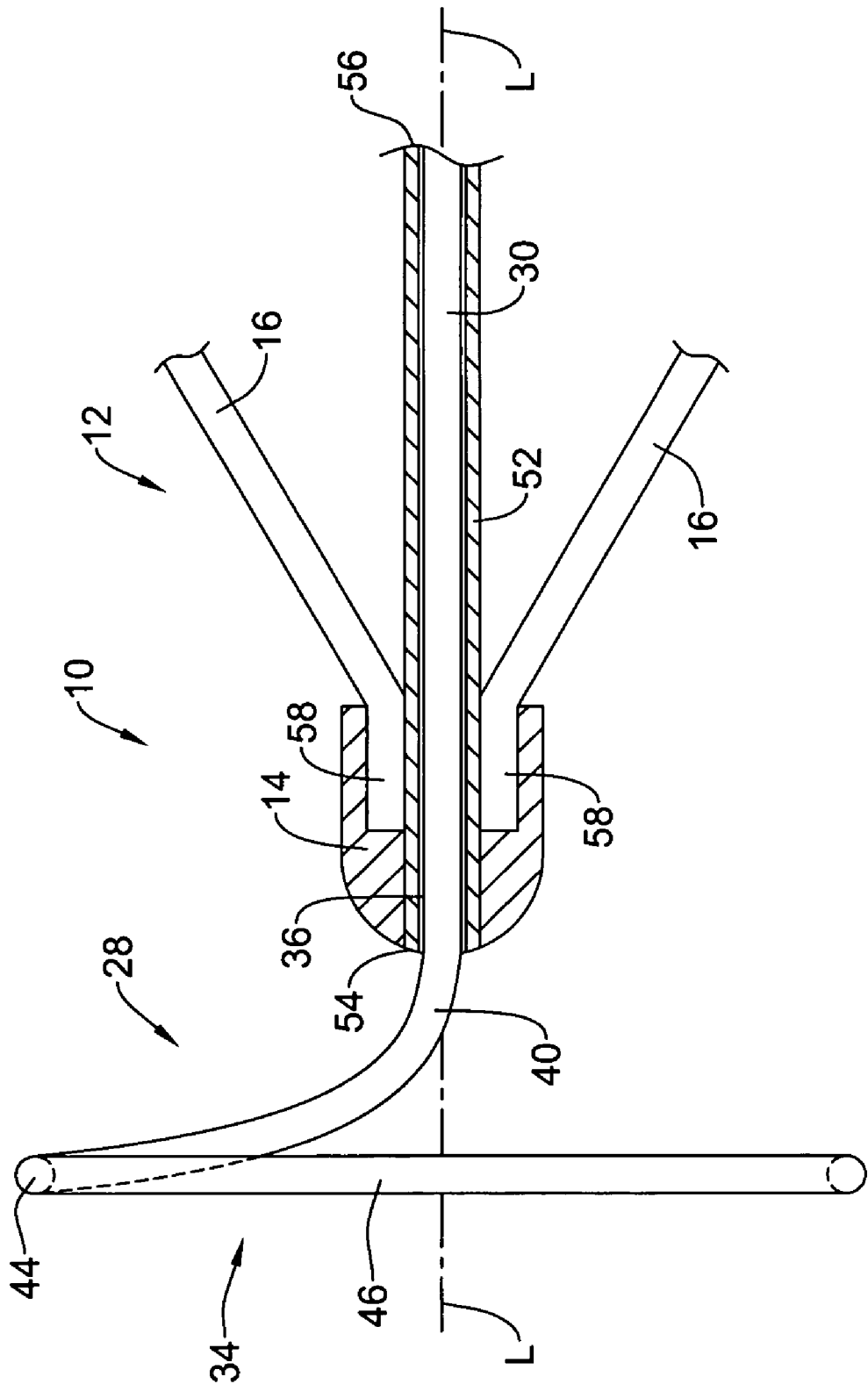
FIG. 2 is a partial cross-sectional view showing the centering member disposed through the apical head of the intravascular filter of FIG. 1.

FIG. 2 is a partial cross-sectional view showing the centering member 28 disposed through the apical head 14 of the intravascular filter 12 of FIG. 1. As shown in FIG. 2, the apical head 14 may include a tubular member 52 having a distal end 54 and a proximal end 56. The tubular member 52 may comprise a member separate from the apical head 14 (e.g. a hypotube) that is then subsequently attached to the apical head 14, or, in the alternative, may be formed integral with the apical head 14. In certain embodiments, for example, the tubular member 52 and joined end 58 of each filter leg 16 can be soldered together using a solder bead, forming an apical head 14 having a generally bulbous shape. In an alternative technique, the tubular member 52, filter legs 16, and apical head 14 may each be formed as a single piece using a suitable process such as insert molding.

The length of the tubular member 52 can be made sufficient to permit the distal section 34 of the elongated wire 30 to be loaded into the interior lumen 36. The inner diameter of the tubular member 52, in turn, can be made slightly larger than the outer diameter of the elongated wire 30, allowing the elongated wire 30 to move within the interior lumen 36. In use, the tubular member 52 acts to maintain the elongated wire 30 in a substantially straight position within the interior lumen 36 prior to deployment within the blood vessel. The tubular member 52 also acts to straighten the elongated wire 30 when it is pulled back into the filter sheath 24 for subsequent removal from the body.

The elongated wire 30 may be formed from a flexible material that permits it to maintain its preset shape when disposed within the interior lumen 36 of the tubular member 52. Examples of suitable flexible materials may include certain metals, polymers, or metal-polymer compounds. In some embodiments, the elongated wire 30 may include a layer or coating of lubricious material such as HYRDOPASS to facilitate movement of the elongated wire 30 through the tubular member 52 and filter sheath 24, and to reduce trauma to the body caused during deployment of the centering member 28 within the blood vessel. The elongated wire 30 as well as other portions of the filter system 10 may also include an anti-thrombogenic coating such as herapin (or its derivatives), urokinase, or PPack (dextrophenylalanine proline arginine chloromethylketone) to prevent insertion site thrombosis from occurring. An anti-inflammatory agent such as dexamethasone, prednisolone, corticosterone, budesonide, estrogen, sulfasalazine, mesalamine, or any suitable combination or mixture thereof may also be applied to the elongated wire 30, intravascular filter 12 as well as other components of the filter system 10 to prevent inflammation within the blood vessel.

In some embodiments, the elongated wire 30 may be formed from a linear elastic material such as a nickel-titanium alloy, which exhibits the ability to undergo significant bending or flexion without imparting a residual stress to the material. Examples of other suitable linear elastic materials may include, but are not limited to, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc (Cu—Zn), copper-zinc-aluminum (Cu—Zn—Al), copper-zinc-tin (Cu—Zn—Sn), copper-zinc-silicon (Cu—Zn—Si), iron-beryllium (Fe—Be), iron-nickel-titanium-cobalt (Fe—Ni—Ti—Co), iron-platinum (Fe—Pt), indium-thallium (In—TI), iron-manganese (Fe—Mn), nickel-titanium-cobalt (Ni—Ti—Co), and copper-tin (Cu—Sn). In certain embodiments, the elongated wire 30 may be combined with other materials such as stainless steel, platinum, titanium, etc. to form a composite material exhibiting certain desirable characteristics within the body. In certain applications, for example, the linear elastic material may be joined together with a relatively radiopaque material such as platinum (Pt) to increase the radiopacity of the composite member, allowing the centering member 28 to be viewed radiographically with the aid of a fluoroscope.

In another aspect of the present invention, the elongated wire 30 may be formed from a shape-memory material that has been heat treated to impart a shape memory effect to distal section 34, allowing the centering member 28 to be transformed from a substantially straight position to an expanded (i.e. Centering) position when withdrawn from within the tubular member 52. In certain embodiments, for example, the elongated wire 30 may be formed of or otherwise include a shape-memory alloy such as a nickel-titanium alloy (Nitinol) configured to transform from a martensite state to an austenite state at or about body temperature, allowing the centering member 28 to assume a preset shape when exposed to blood within the blood vessel.

Figure 3:
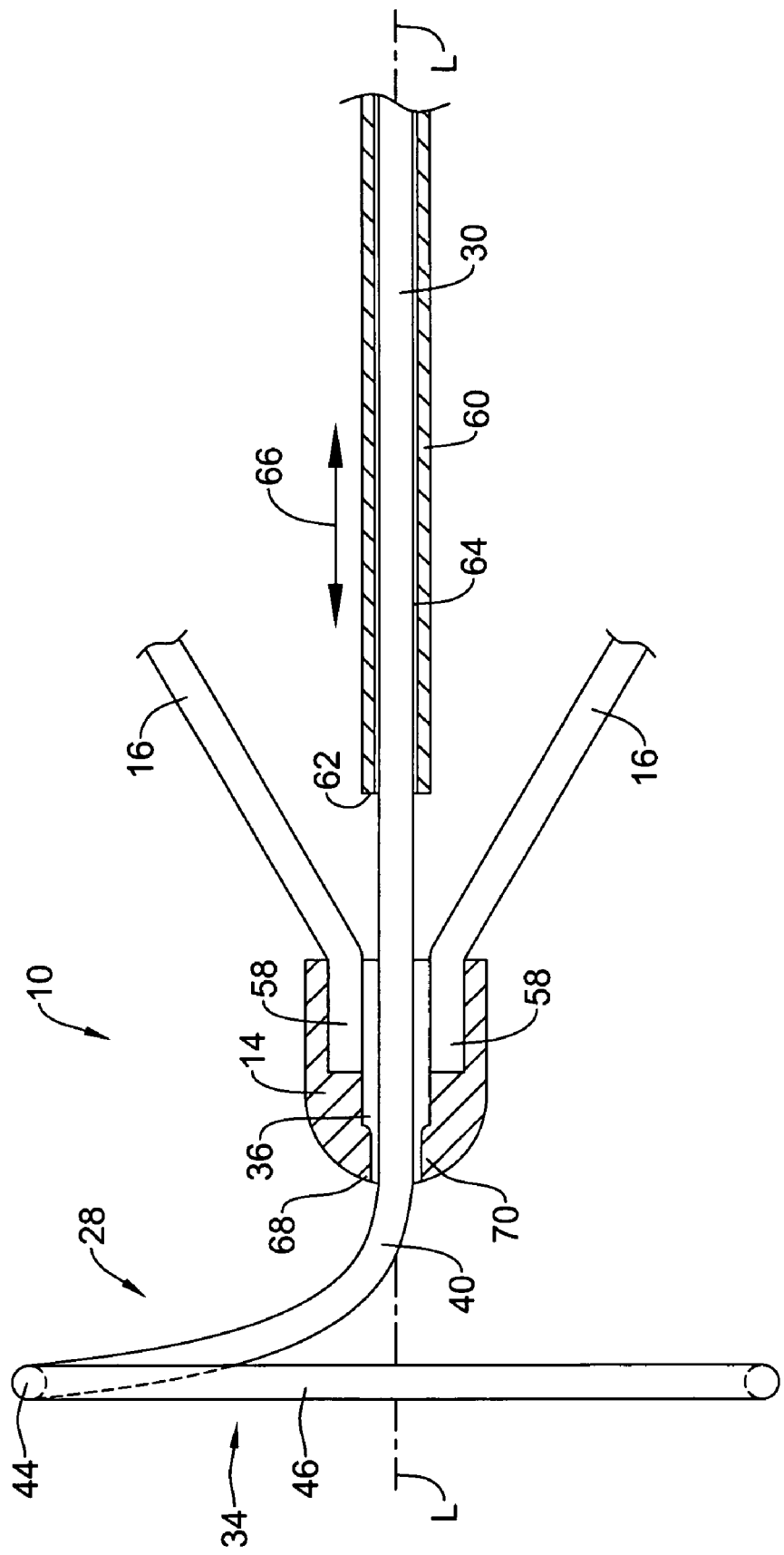
FIG. 3 is a partial cross-sectional view showing an alternative embodiment employing a tubular member movably disposed relative to the intravascular filter.

FIG. 3 is a partial cross-sectional view showing an alternative embodiment employing a tubular member 60 movably disposed relative to the intravascular filter 12. As shown in FIG. 3, the tubular member 60 has a distal end 62, a proximal end (not shown), and an interior lumen 64 therethrough adapted slidably receive the distal section 34 of centering member 28 in a manner similar to that described above with respect to FIG. 2. As indicated by the arrow 66, however, the tubular member 60 can be configured to move independently of the intravascular filter 12, allowing the physician to further remove the tubular member 60 from the body once the intravascular filter 12 has been deployed within the blood vessel. The tubular member 60 can be either connected to the filter sheath 24, or can be configured to independently move within the interior lumen 22 of the filter sheath 24.

The interior lumen 36 of the apical head 14 can be sized to slidably receive the tubular member 60 to facilitate advancement of the centering member 28 distally beyond the distal end 68 of the apical head 14. If desired, a tapered inner portion 70 of the apical head 14 extending inwardly into the interior lumen 36 can be configured to prevent the physician from overextending the distal end 62 of the tubular member 60 beyond the distal end 68 of the apical head 14. In use, the tapered inner portion 70 acts as a distal stop as the physician advances the tubular member 60 through the interior lumen 36, preventing the tubular member 60 from being advanced distally beyond the distal end 68 of the apical head 14. In some cases, the tapered inner portion 70 may also provide the physician with tactile feedback that the centering member 28 is in the proper position within the interior lumen 36 for deployment.

Figure 4:
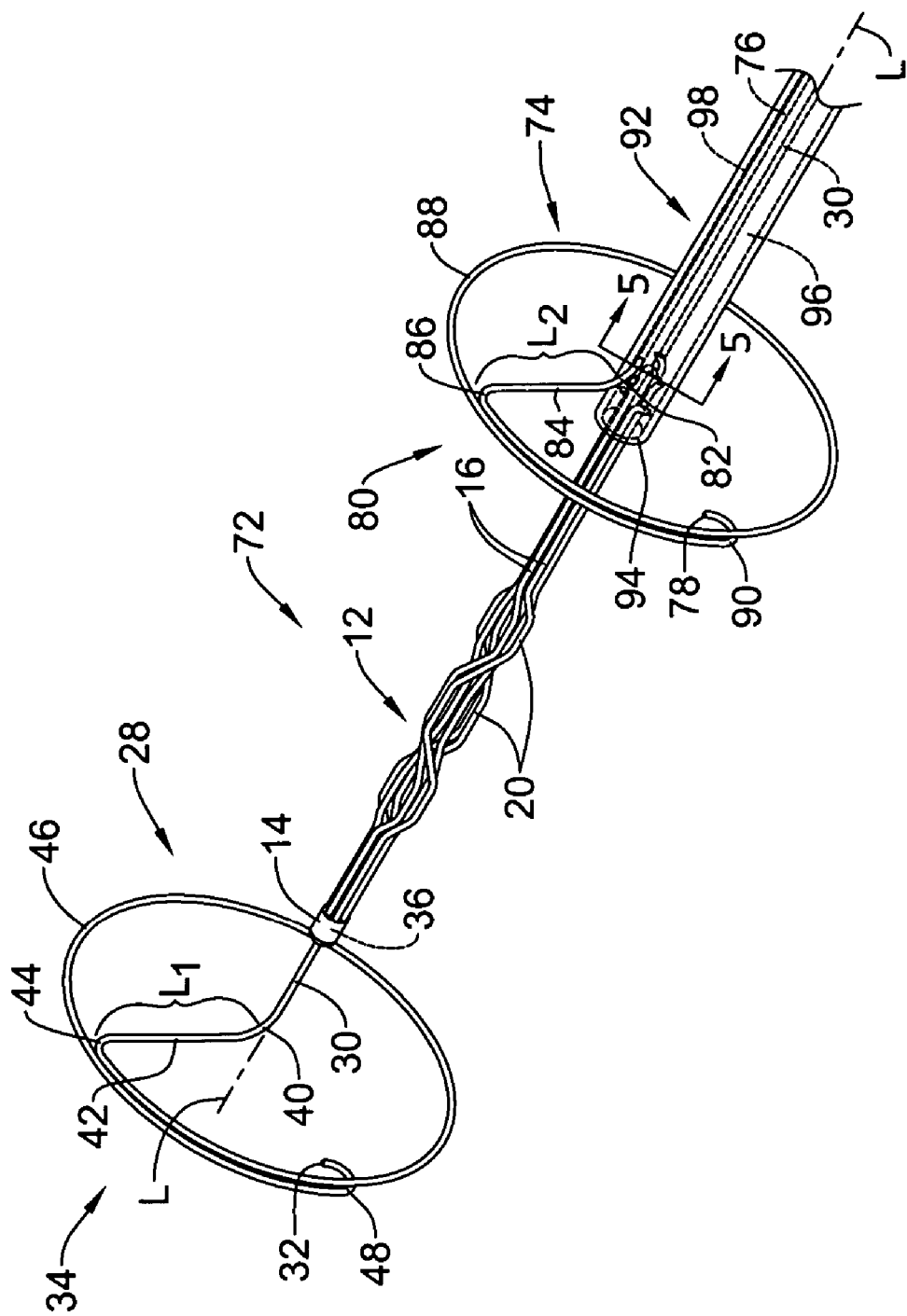
FIG. 4 is a perspective view of a filter system in accordance with an illustrative embodiment of the present invention employing multiple centering members.

FIG. 4 is a perspective view of a filter system 72 in accordance with another illustrative embodiment of the present invention employing two centering members. Filter system 72 may be configured similar to filter system 10 described above with respect to FIGS. 1-2, with like elements being labeled in like fashion. In the illustrative embodiment of FIG. 4, however, the filter system 72 may further include a second centering member 74 that can be used to aid in centering the base of the intravascular filter 12 within the blood vessel.

The second centering member 74 may comprise an elongated wire 76 having a distal end 78, a proximal end (not shown), and a distal section 80 adapted to assume a preset shape when deployed within the blood vessel. In a generally deployed position illustrated in FIG. 4, the distal section 80 may comprise a portion of the elongated wire 76 extending distally from a first bend region 82 to the distal end 78 thereof. A radial section 84 of the elongated wire 76 extending distally from the first bend region 82 can be adapted to extend outwardly in a direction substantially orthogonal to the interior wall of the blood vessel, when deployed. As with the first centering member 28, the length $L_2$ of the radial section 84 may vary depending on the size of the blood vessel. The length $L_2$ of the radial section 84 may be made similar to the length $L_1$ of radial section 42, or may be made grater or lesser than length $L_1$.

At a second bend region 86 of the distal section 80, the elongated wire 76 may transition to a hoop section 88 of the elongated wire 76 extending circumferentially about the longitudinal axis L. The shape of the hoop section 88 can be selected to approximate the general shape of the blood vessel, similar to that described above with respect to the other centering member 28. Other features such as a third bend region 90 forming a curled (i.e. atraumatic) distal end 78 may also be provided, if desired.

Figure 5:
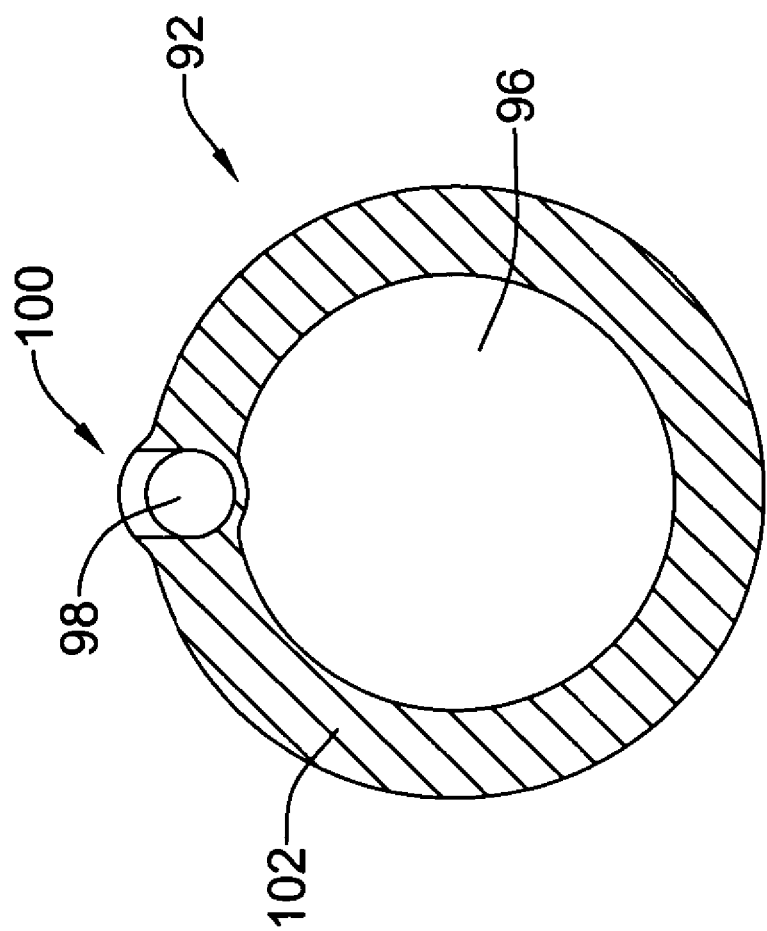
FIG. 5 is a transverse cross-sectional view of the filter sheath along line 5-5 in FIG. 4.

The filter system 72 may further include a filter sheath 92 having a distal end 94, a proximal end (not shown), and an interior lumen 96 therethrough adapted to slidably receive the intravascular filter 12 and a portion of the elongated wire 30. A second interior lumen 98 of the filter sheath 92, in turn, can be adapted to slidably receive the second elongated wire 76, allowing the physician to deploy the second centering member 74 within the blood vessel at a location at or near the distal end 94 of the filter sheath 92. As can be seen in further detail in FIG. 5, a lumen opening 100 provided in the wall 102 of the filter sheath 92 may form an exit port, allowing the physician to advance the second elongated wire 76 distally out from within the second interior lumen 98 to deploy the second centering member 74 within the blood vessel.

Figure 6:
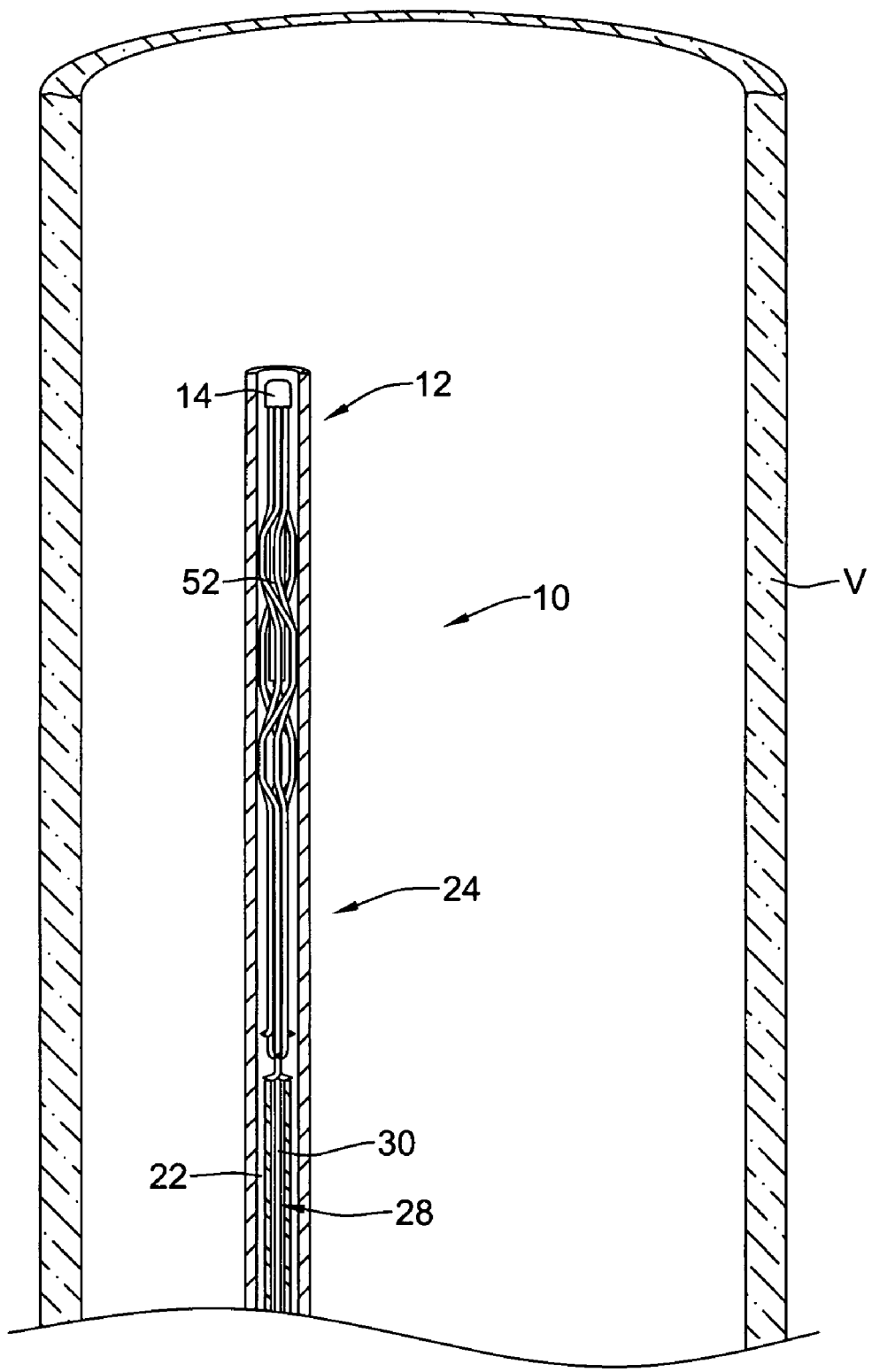
FIG. 6 is a partial cross-sectional view showing the illustrative filter system of FIG. 1 in a first position within a blood vessel.

Referring now to FIGS. 6-9, an illustrative method of centering an intravascular filter in accordance with the present invention will now be described with respect to filter system 10 described above. In a first position illustrated in FIG. 6, the intravascular filter 12 and centering member 28 are shown loaded into the interior lumen 22 of the filter sheath 24 and advanced to a desired location within a blood vessel V (e.g. the superior or inferior vena cava). As shown in FIG. 6, the centering member 28 can be configured to maintain a substantially straight shape when radially constrained within the interior lumen 36 of the tubular member 52. Such straight shape permits the filter system 10 to assume a relatively small profile when transported through the vasculature, allowing the physician to employ a smaller sized filter sheath 24.

Once the filter system 10 is advanced to a desired location within the blood vessel V, the physician may next advance the elongated wire 30 distally out from within the interior lumen 36, causing the distal section 34 of the elongated wire 30 to assume its preset shape within the blood vessel V. The elongated wire 30 can be deployed within the blood vessel V by holding the filter sheath 24 and intravascular filter 12 stationary while advancing the elongated wire 30 distally, or, in the alternative, by holding the elongated wire 30 stationary and retracting the filter sheath 24 and intravascular filter 12 proximally. A combination of the two techniques may also be performed to deploy the centering member 28, if desired.

Figure 7:
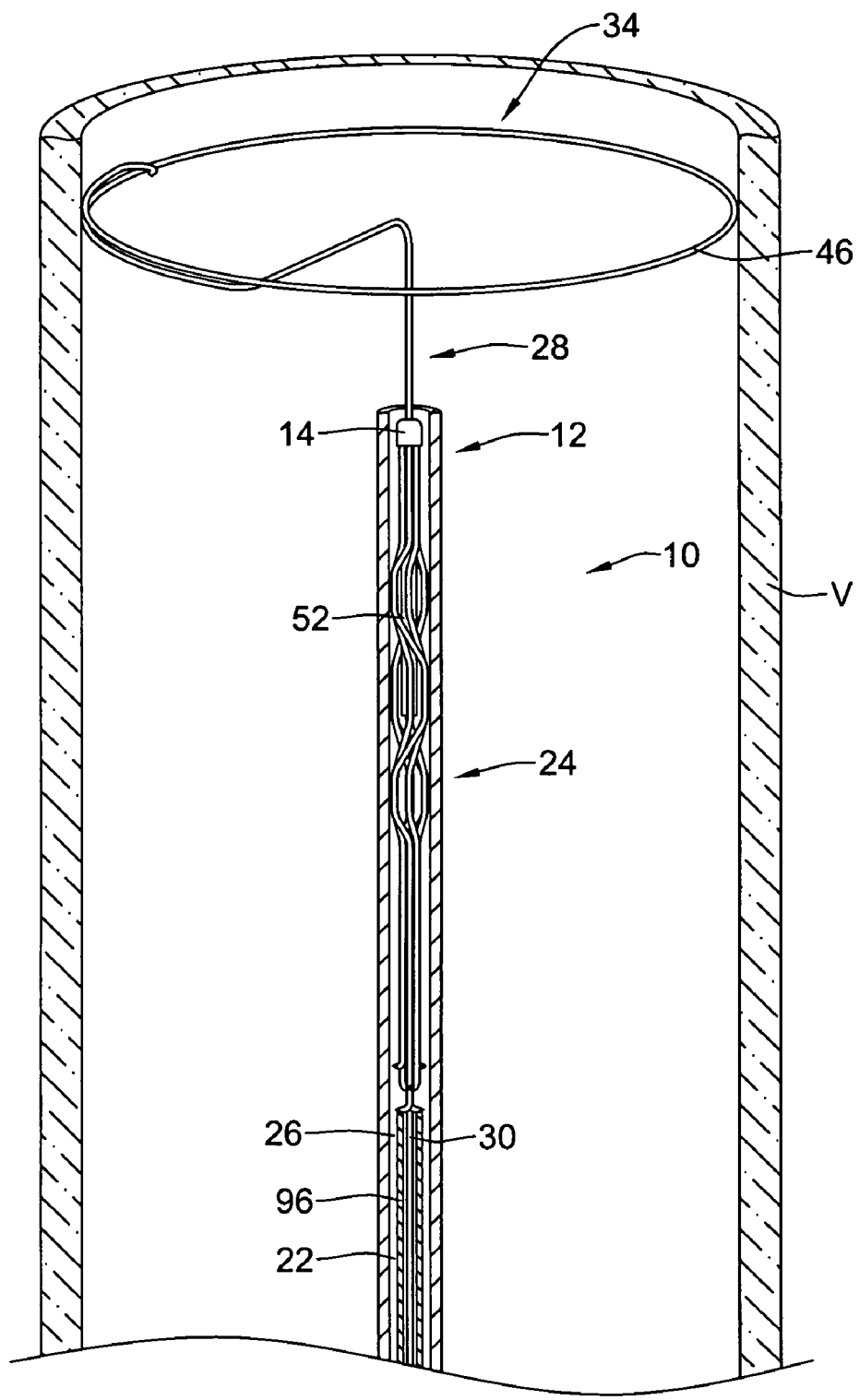
FIG. 7 is a partial cross-sectional view showing the illustrative filter system of FIG. 1 in a second position within the blood vessel, wherein the centering member is shown engaged against the vessel wall.

Once the centering member 28 is withdrawn from the tubular member 52, the hoop section 46 can be configured to radially expand and fully appose the vessel wall, as shown, for example, in FIG. 7. When this occurs, a centering force is exerted against the apical head 14 by the elongated wire 30, causing the intravascular filer 12 to align centrally within the blood vessel V. If, for example, the filter system 10 is off-centered within the blood vessel V (see FIG. 6), the general alignment of the elongated wire 30 centrally within the blood vessel V produces a centering force that re-aligns the intravascular filter 12 within the blood vessel V.

Figure 8:
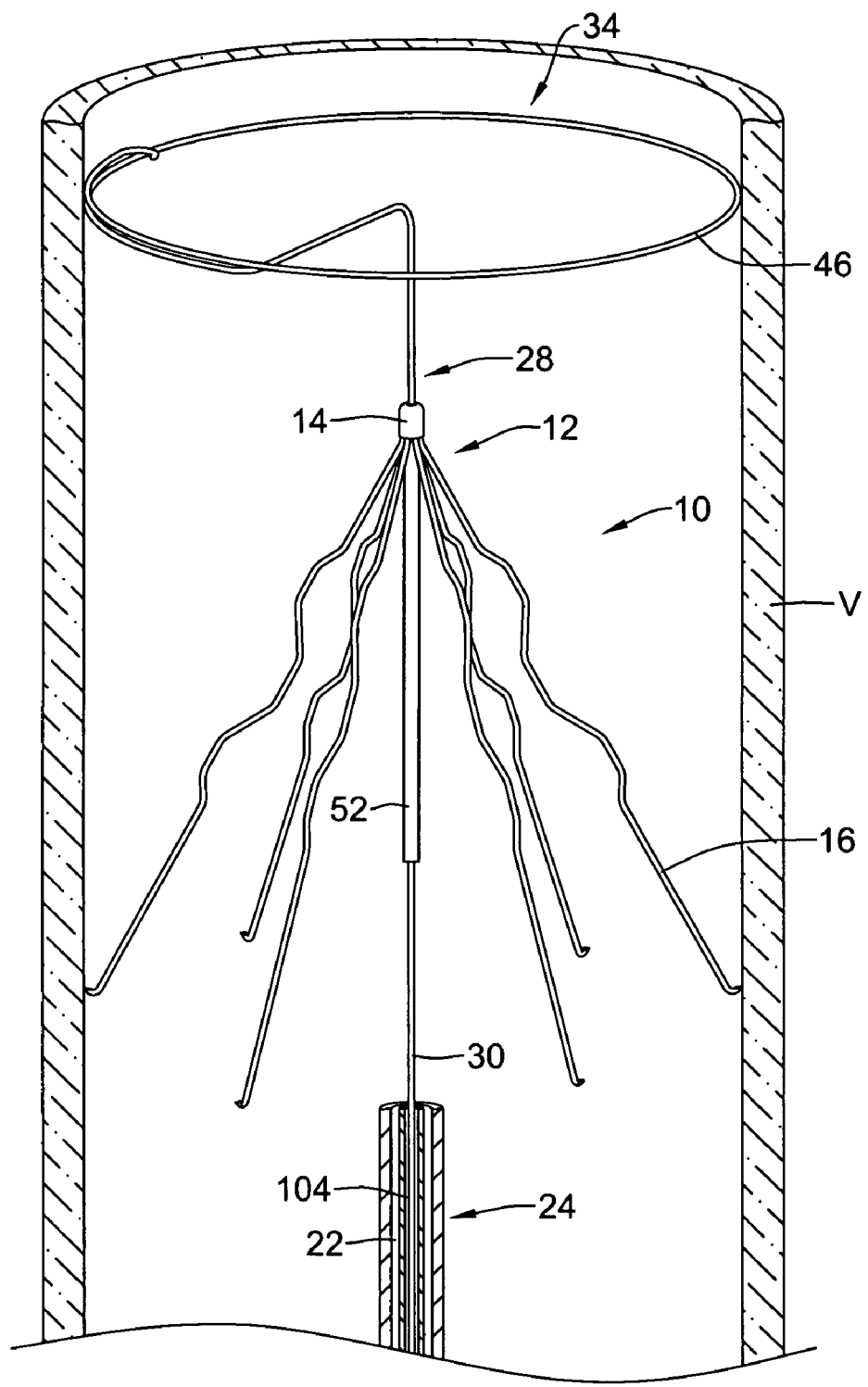
FIG. 8 is a partial cross-sectional view showing the illustrative filter system of FIG. 1 in a third position within the blood vessel, wherein the intravascular filter is shown deployed within the blood vessel.
Figure 9:
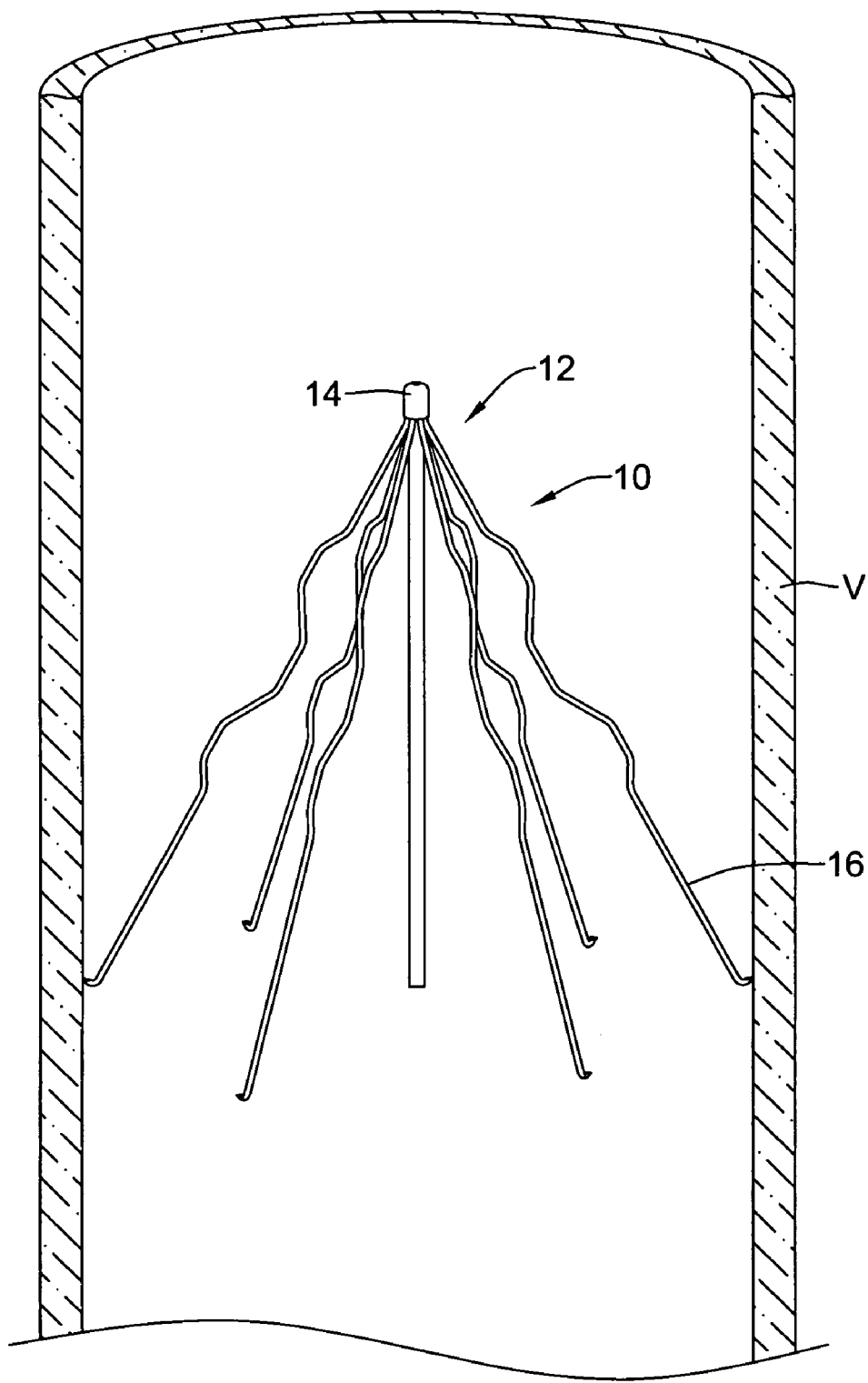
FIG. 9 is a partial cross-sectional view showing the illustrative filter system of FIG. 1 in a fourth position within the blood vessel, wherein the centering member and delivery catheter are shown removed from the blood vessel.
Figure 10:
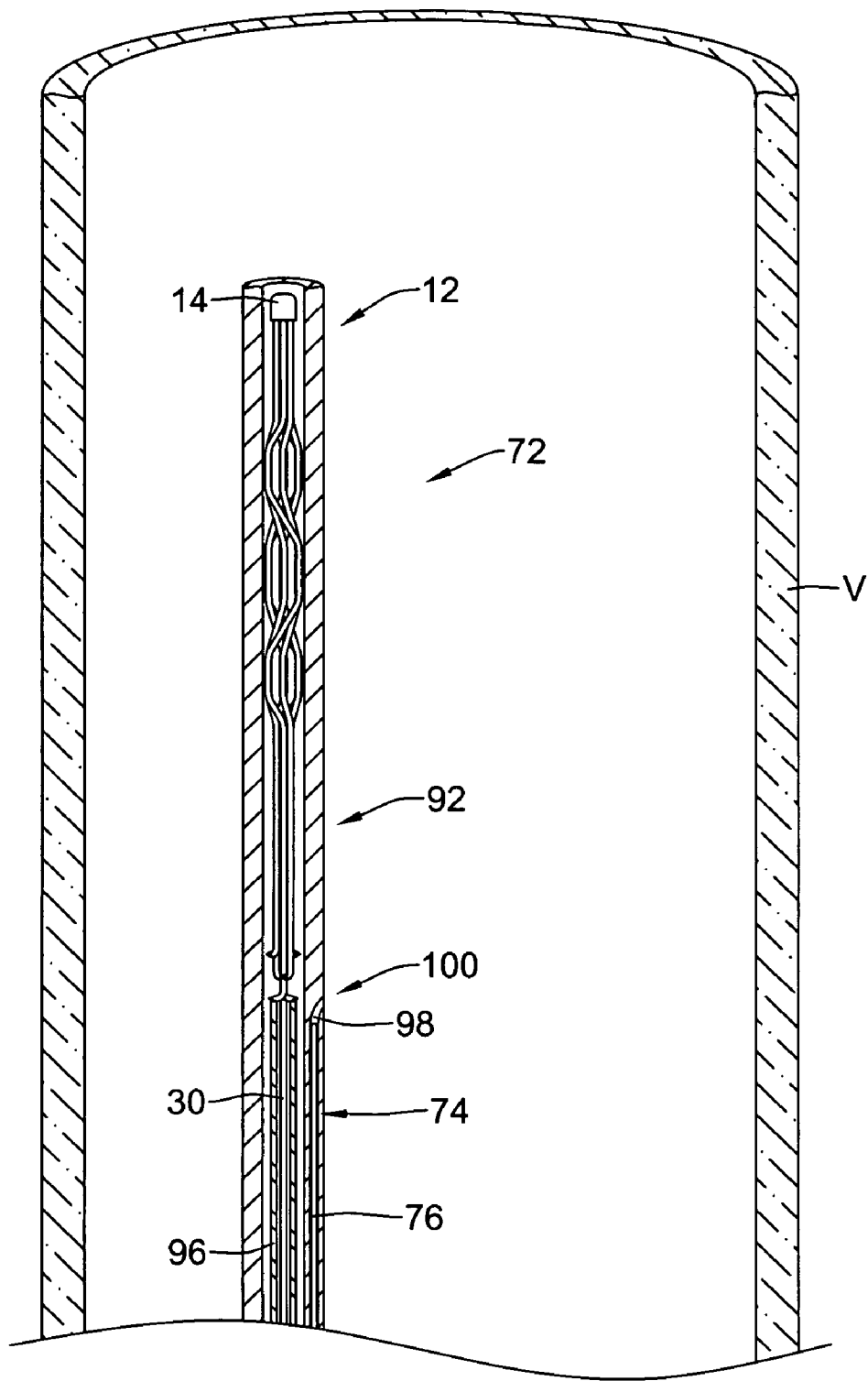
FIG. 10 is a partial cross-sectional view showing the illustrative filter system of FIG. 4 in a first position within a blood vessel.

To deploy the intravascular filter 12 within the blood vessel V, the physician, while holding the elongated wire 30 stationary, may next retract the filter sheath 24 in the proximal direction to expose the filter legs 16, as shown, for example, in FIG. 8. If desired, a pusher tube 104 can be provided within the interior lumen 22 of the filter sheath 24 to hold the intravascular filter 12 stationary as the filter sheath 24 is being retracted proximally. Once the intravascular filter 12 is deployed within the blood vessel V, the physician may next pull the elongated wire 30 proximally through the tubular member 52 and out of the body, if desired. As shown in a subsequent view in FIG. 9, the filter sheath 24 and centering member 28 can then be removed from the body, leaving the centered intravascular filter 12 within the blood vessel V.

Turning now to FIGS. 10-14, another illustrative method of centering an intravascular filter in accordance with the present invention will now be described with respect to filter system 72 described above. In a first position illustrated in FIG. 10, the intravascular filter 12, first centering member 28, and second centering member 74 are shown loaded into the filter sheath 92 and advanced to a desired location within a blood vessel V (e.g. the inferior vena cava).

Once the filter system 72 is advanced to a desired location within the blood vessel V, the physician may next advance the second elongated wire 76 distally out from the second interior lumen 98 through the lumen opening 100. Once the centering member 74 is deployed within the blood vessel V, the hoop section 88 can be configured to radially expand and fully appose the vessel wall, as shown, for example, in FIG. 11. When this occurs, the centering force of the elongated wire 76 exerted against the filter sheath 92 causes the filter sheath 92 to align centrally within the blood vessel V.

Figure 12:
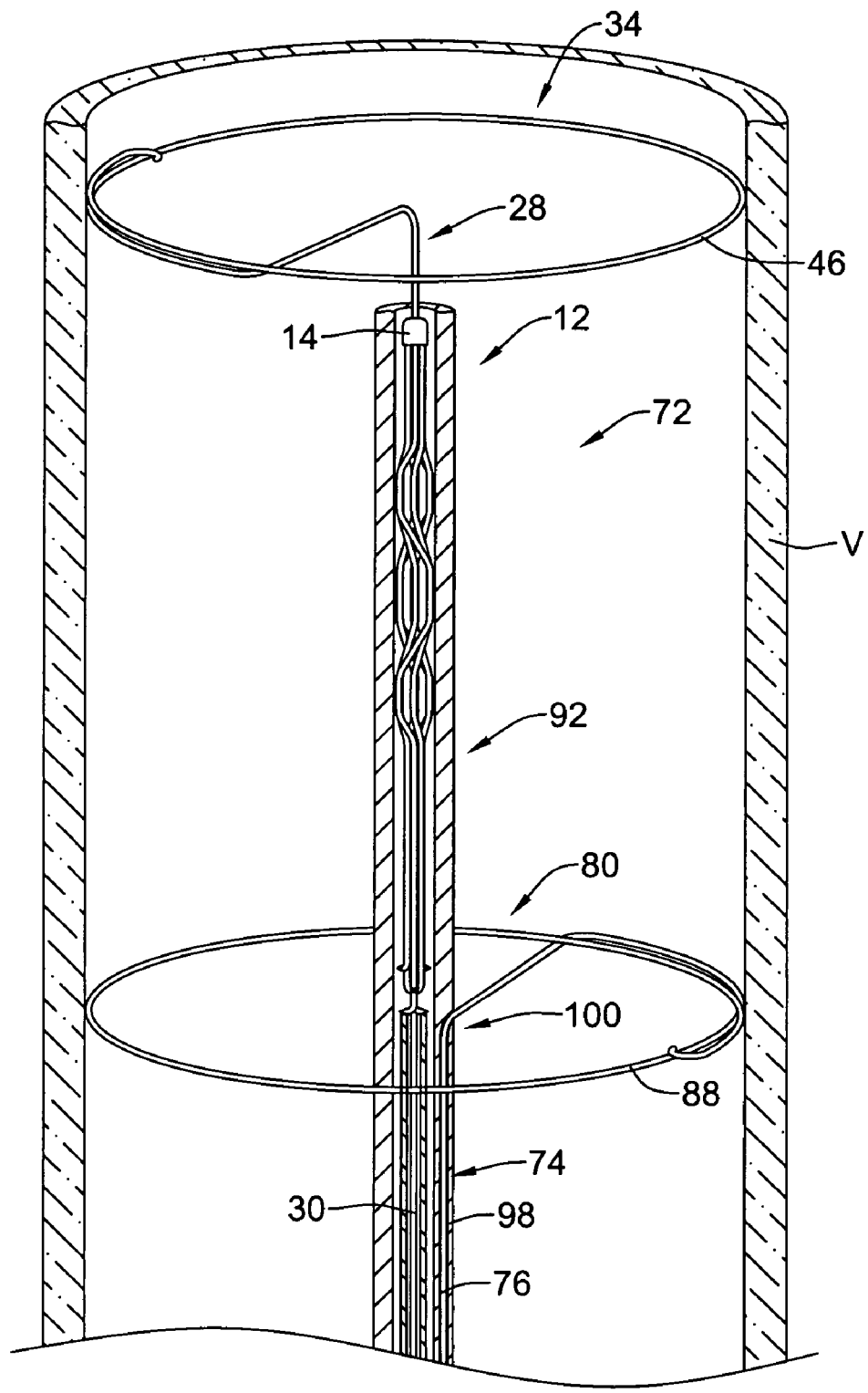
FIG. 12 is a partial cross-sectional view showing the illustrative filter system of FIG. 4 in a third position within the blood vessel, wherein the first and second centering members are shown engaged against the vessel wall.
Figure 13:
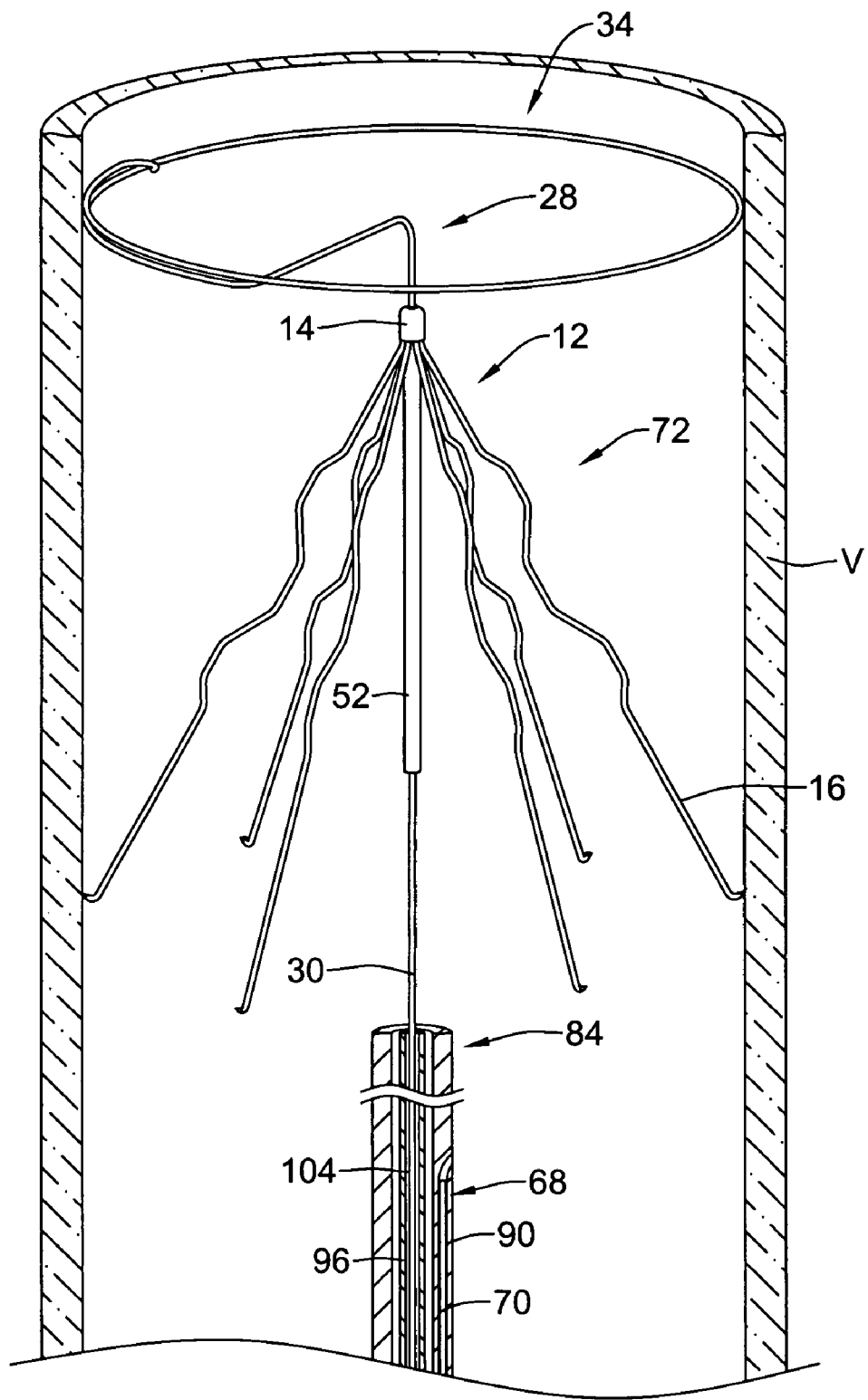
FIG. 13 is a partial cross-sectional view showing the illustrative filter system of FIG. 4 in a fourth position within the blood vessel, wherein the intravascular filter is shown deployed within the blood vessel.

In addition to deploying the second centering member 74 within the blood vessel V, the physician may further advance the first elongated wire 30 distally out from within the interior lumen 36, causing the distal section 34 of the elongated wire 30 to assume its preset shape within the blood vessel V, as shown, for example, in FIG. 12.

To deploy the intravascular filter 12 within the blood vessel V, the physician may next retract the second elongated wire 76 proximally within the filter sheath 92, causing the distal section 80 to straighten within the second interior lumen 98. The physician, while holding the first elongated wire 30 stationary, may also retract the filter sheath 92 proximally to expose the filter legs 16, as shown, for example, in FIG. 13. If desired, a pusher tube 104 can be provided within the interior lumen 96 of the filter sheath 92 to hold the intravascular filter 12 stationary as the filter sheath 92 is being retracted. Once the intravascular filter 12 is deployed within the blood vessel V, the physician may next pull the elongated wire 30 proximally through the tubular member 52. The filter sheath 92 and centering members 28, 74 can then be removed from the body, leaving the centered intravascular filter 12 within the blood vessel V.

Figure 11:
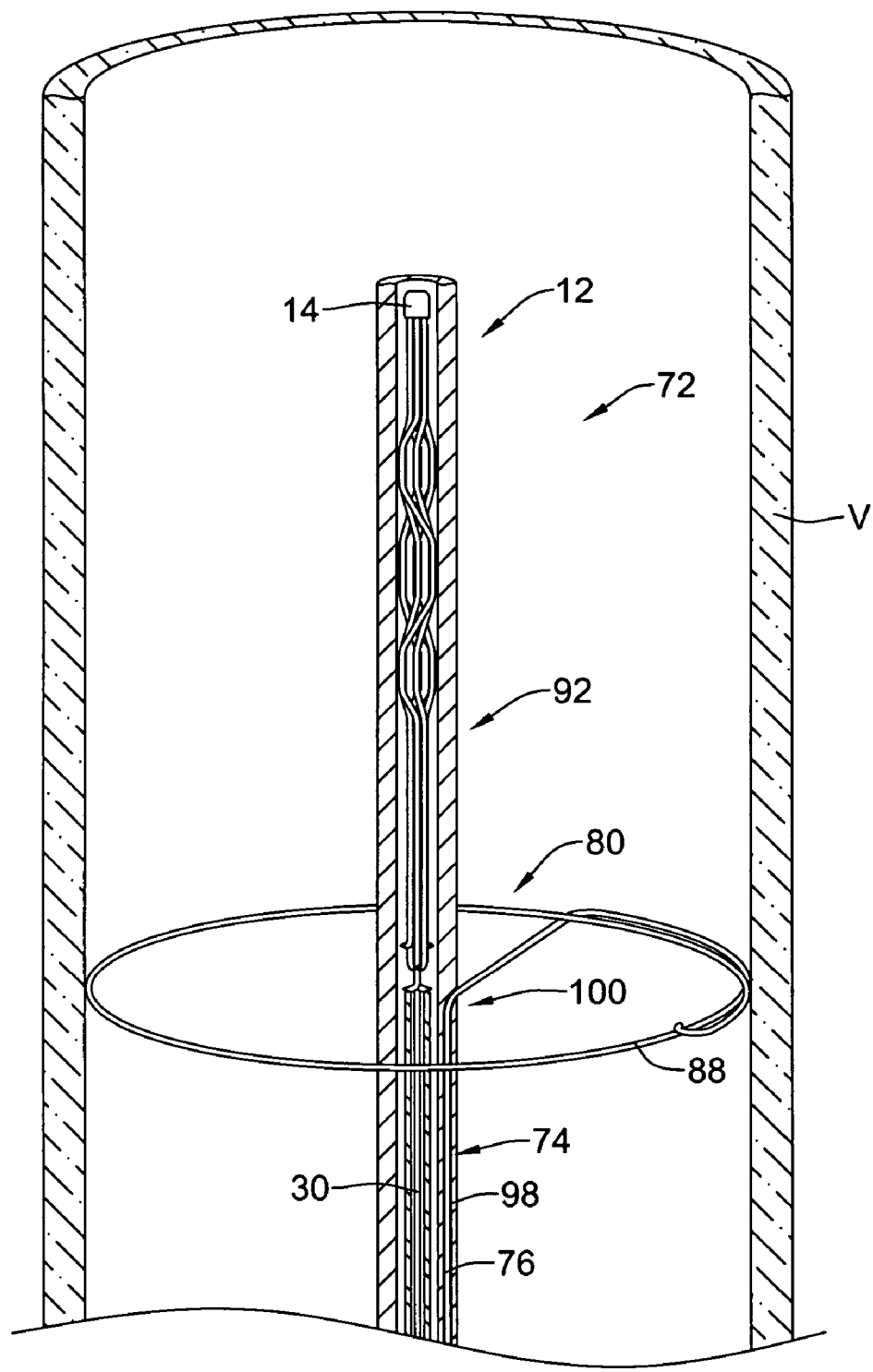
FIG. 11 is a partial cross-sectional view showing the illustrative filter system of FIG. 4 in a second position within the blood vessel, wherein the second centering member is shown engaged against the vessel wall.

While the illustrative steps depicted in FIGS. 11-12 show the deployment of the second centering member 74 prior to the first centering member 28, other embodiments have been envisioned wherein the first centering member 28 is deployed prior to the second centering member 74, or wherein both centering members 28, 74 are deployed at or about the same time.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes can be made with respect to various elements described herein without exceeding the scope of the invention.

What is claimed is:

1. A filter system, comprising:
  an intravascular filter including a plurality of elongated filter legs operatively coupled to an apical head;
  wherein the apical head has a proximal end and a distal end;
  wherein the elongated filter legs extend proximally of the proximal end of the apical head when the filter is deployed within a blood vessel;
  a filter sheath having a first end, a proximal end, and an interior lumen adapted to contain the intravascular filter; and
  a centering hoop including an elongated wire adapted to assume a preset shape when deployed within a blood vessel, wherein the centering hoop is disposed distally of the distal end of the apical head and radially expands against the inner wall of the blood vessel when the filter is deployed;

wherein the centering hoop is slidably disposed within an interior lumen of the apical head;

wherein the elongated wire includes a first end and a proximal end;

wherein the preset shape of the elongated wire includes a radial section and a hoop section, the hoop section extending circumferentially at least one full revolution about a generally longitudinal axis of the intravascular filter and filter sheath.

2. The filter system of claim 1, wherein, during deployment, the radial section of the elongated wire is adapted to extend outwardly in a direction substantially orthogonal to the interior wall of the blood vessel.

3. The filter system of claim 1, wherein the hoop section of the elongated wire has a circular shape.

4. The filter system of claim 1, wherein the hoop section of the elongated wire has an elliptical shape.

5. The filter system of claim 1, wherein the first end of the elongated wire is curled.

6. The filter system of claim 1, further comprising a tubular member having an interior lumen adapted to contain the centering hoop in a substantially straight position.

7. The filter system of claim 6, wherein the tubular member is coupled to the apical head.

8. The filter system of claim 6, wherein the tubular member is movably disposed relative to the intravascular filter.

9. The filter system of claim 8, wherein the tubular member is coupled to the filter sheath.

10. The filter system of claim 6, wherein the tubular member comprises a hypotube.

11. The filter system of claim 1, wherein the centering hoop is formed from a flexible material.

12. The filter system of claim 11, wherein said flexible material is a linear elastic material.

13. The filter system of claim 11, wherein said flexible material is a shape-memory material.

14. The filter system of claim 1, further comprising a second centering hoop including a second elongated wire adapted to assume a preset shape when deployed within the blood vessel, said second elongated wire having a first end and a proximal end.

15. The filter system of claim 14, wherein the preset shape of the second elongated wire includes a radial section and the hoop section.

16. A filter system, comprising:

an intravascular filter including a plurality of elongated filter legs operatively coupled to an apical head;

wherein the apical head has a proximal end and a distal end;

wherein the elongated filter legs extend proximally from the proximal end of the apical head when the filter is deployed within a blood vessel;

a filter sheath having a first end, a proximal end, and an interior lumen adapted to contain the intravascular filter; and an elongated wire slidably disposed within an interior lumen of the apical head and including a first end, a proximal end, and a first section adapted to assume a preset shape when deployed within a blood vessel, said preset shape including a radial section and a hoop section, wherein the hoop section is disposed distally of the distal end of the apical head and radially expands against the inner wall of the blood vessel when the filter is deployed and the hoop section extends circumferentially at least one full revolution about a generally longitudinal axis of the intravascular filter and filter sheath.

17. The filter system of claim 16, wherein, during deployment, the radial section of the elongated wire is adapted to extend outwardly in a direction substantially orthogonal to the interior wall of the blood vessel.

18. The filter system of claim 16, wherein the hoop section of the elongated wire has a circular shape.

19. The filter system of claim 16, wherein the hoop section of the elongated wire has an elliptical shape.

20. The filter system of claim 16, wherein the distal end of the elongated wire is curled.

21. The filter system of claim 16, further comprising a tubular member having an interior lumen adapted to contain the centering member in a substantially straight position.

* * * * *